United States Patent [19]

Sarantakis

[11] 4,182,707

[45] Jan. 8, 1980

[54] SOMATOSTATIN ANALOGUES

[75] Inventor: Dimitrios Sarantakis, West Chester, Pa.

[73] Assignee: American Home Products Corporation, New York, N.Y.

[21] Appl. No.: 920,109

[22] Filed: Jun. 28, 1978

[51] Int. Cl.² ..................... C07C 103/52; A61K 37/00
[52] U.S. Cl. ............................. 260/112.5 S; 424/177
[58] Field of Search ................. 260/112.5 S; 424/177

[56] References Cited

U.S. PATENT DOCUMENTS

| 4,061,626 | 4/1976 | Shields | 260/112.5 S |
| 4,087,390 | 5/1978 | Shields | 260/112.5 S |

OTHER PUBLICATIONS

Peptides 1976, 14th European Peptide Symposium, Apr. 11-17, 1976, discloses in Table III, p. 439.

*Primary Examiner*—Delbert R. Phillips

*Attorney, Agent, or Firm*—Richard K. Jackson

[57] ABSTRACT

Polypeptides of the formula:

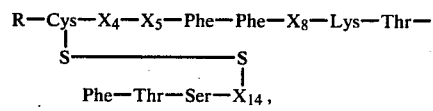

the linear precursors, intermediates and non-toxic acid addition salts thereof, wherein R is hydrogen, Ala-Gly, Ala-D-Ala, Gly-Gly, Gly-Gly-Gly, lower alkanoyl or benzoyl;

$X_4$ is D-Lys, D-Arg, D-His or D-Orn;

$X_5$ is Trp, Phe, Tyr, Leu or Met;

$X_8$ is L-Trp or D-Trp; and $X_{14}$ is Cys or D-cys are described. These polypeptides inhibit the secretion of growth hormone.

5 Claims, No Drawings

SOMATOSTATIN ANALOGUES

DESCRIPTION OF THE INVENTION

In accordance with this invention there is provided a group of polypeptides of the following formula:

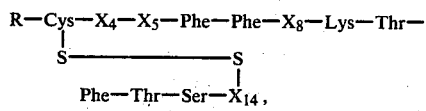

the linear precursors, intermediates and non-toxic acid addition salts thereof, in which R is hydrogen, Ala-Gly, Ala-D-Ala, Gly-Gly, Gly-Gly-Gly, lower alkanoyl or benzoyl; $X_4$ is D-Lys, D-Arg, D-His or D-Orn; $X_5$ is Trp, Phe, Tyr, Leu or Met; $X_8$ is L-Trp or D-Trp and $X_{14}$ is Cys or D-Cys. These compounds inhibit the secretion of growth hormone selectively at relatively high doses and like somatostatin are useful in the treatment of diabetes mellitis and acromegaly.

The polypeptides of this invention are distinguished by the basic, hydrophilic nature of the amino acids of the D-series in 4-position and the hydrophobic amino acids in the 5-position in lieu of the hydrophilic amino acid asparagine found in somatostatin itself.

The polypeptides are produced by the well known solid phase method as described by Stewart et al., Solid Phase Peptide Synthesis, Freeman and Co., San Francisco, 1969. As applied to the compounds of this invention, α-amino and sulfhydryl protected cysteine is attached to a chloromethylated polystyrene resin followed by removal of the α-amino protecting group with trifluoroacetic acid in methylene chloride, trifluoroacetic acid alone or HCl in dioxane. The deprotection is conducted at a temperature between about 0° C. and room temperature. Other standard cleaving reagents and conditions for removal of specific α-amino protecting groups may be used as described in Schroder E. Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in the desired order. Each protected maino acid or amino acid sequence is introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The coupling reagent employed was diisopropylcarbodiimide.

After the desired amino acid sequence has been synthesized, the polypeptide is removed from the resin support by treatment with hydrogen fluoride and anisole to obtain the fully deprotected linear polypeptide. The cyclic disulfide is produced by air oxidation or potassium ferricyanide ($K_3Fe(CN)_6$).

The ultimate fully protected, resin bound polypeptide of this invention specifically exemplified infra is tert-Buthloxycarbonyl-S-p-methoxybenzyl-L-cysteinyl-N$^\epsilon$-2-chlorobenzyloxycarbonyl-D-lysyl-L-tryptophyl-L-phenylalanyl-L-phenylalanyl-D-tryptophyl-N$^\epsilon$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl-polystyrene.

Non-toxic acid addition salts of the linear and cyclic polypeptides are produced by methods well known in the art from hydrochloric, hydrobromic, sulfuric, phosphoric, polyphosphoric, maleic, acetic, citric, benzoic, succinic, malonic or ascorbic acid and the like.

The protecting groups employed throughout the solid phase synthesis are well known to the art. The α-amino protecting groups employed with each amino acid introduced in sequence of the ultimate polypeptide are of the (1) acyl type protecting groups illustrated by the following: formyl, trifluoroacetyl, phthalyl, p-toluenesulfonyl (tosyl), nitrophenylsulfenyl, etc.; (2) aromatic urethane type protecting groups illustrated by benzylocycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethane protecting groups illustrated by tert-butyloxycarbonyl, diisopropylmethoxycarbonyl, isopropyloxycarbonyl, alyloxycarbonyl, 2,2,2-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as trimethylsilane. The preferred α-amino protecting group is tert-butyloxycarbonyl.

Protection for the phenolic hydroxyl group, in amino acids such as D-tyrosine, may be by benzyl, 2,6-dichlorophenyl, benzyloxycarbonyl, 2-bromobenzyloxycarbonyl and the like.

Protection for the side chain amino group of amino acids such as lysine and ornithine, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

Protection for the hydroxyl group of threonine and serine may be with the acetyl, benzoyl, tert-butyl, benzyl. The benzyl group is preferred for this purpose.

The protecting group for the sulfhydryl group of the cysteinyl amino acid residue is a group selected from the class consisting of benzyl; substituted benzyl wherein the substituent is at least one of methyl, methoxy, nitro, or halo (e.g. 3,4-dimethylbenzyl, p-methoxybenzyl, p-chlorobenzyl, p-nitrobenzyl, (etc.); trityl, benzyloxycarbonyl, benzhydryl, p-methoxybenzyloxycarbonyl, benzylthiomethyl, ethylcarbamoyl, thioethyl, tetrahydropyranyl, acetamidomethyl, benzoyl, s-sulfonate salt, etc; the p-methoxybenzyl group being preferred.

Protection of the side chain nitrogen atom(s) of D-arginine (N$^g$) may be by nitro, tosyl, benzyloxycarbonyl, adamantyloxycarbonyl and trityl groups with the tosyl group preferred.

Protection of the imidazole nitrogen of D-histidine (N$^{im}$) may be by tosyl, benzyl, trityl, benzyloxycarbonyl groups with the tosyl group preferred.

In selecting a particular side chain protecting group to be used in the synthesis of the peptides of this invention, the following rules should be followed: (a) The side chain protecting group must be stable to the reagent and under the reaction conditions selected for removing the α-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

The following Example illustrates the preparative technique applicable in the production of the compounds of this invention. By introducing tert-butyloxycarbonyl S-p-methoxybenzyl-D-cysteine as the first amino acid attached to the resin, the D-Cys-OH compounds result. Similarly, by introducing tert-butyloxycarbonyl protected D-tryptophan into the solid phase reactor as the seventh amino acid introduced, the compounds corresponding to D-Trp as $X_8$ in the generic formula, supra, are produced. Similarly by introducing tert-butyloxycarbonyl protected phenylalanine, tyrosine(O-2,6-dichlorobenzyl), leucine or methionine into the solid phase reactor as the tenth amino acid, there is obtained the corresponding polypeptide varied in the $X_5$-position. And, by introducing tert-butyloxycarbonyl protected D-arginine ($N^g$-tosyl), D-histidine (N-tosyl) or D-ornithine (N-2-chlorobenzyloxycarbonyl) as the eleventh amino acid, there is obtained the corresponding polypeptide varied in the $X_4$-position.

Likewise, by omitting the sequential introduction of t-butyloxycarbonyl-Gly-OH as the thirteenth amino acid and t-butyloxycarbonyl-Ala-OH as the fourteenth member of the sequence affords, after complete deprotection, a dodecapeptide of the formula:

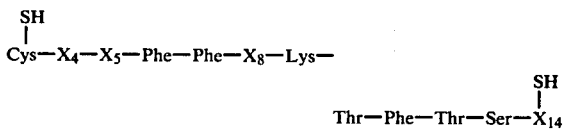

in which $X_4$ is D-Lys, D-Arg, D-His or D-Orn; $X_5$ is Trp, Phe, Tyr, Leu or Met; $X_8$ is L-Trp or D-Trp and $X_{14}$ is Cys or D-Cys. All undesignated optically active amino acids are of the L-series, which linear intermediate is readily cyclized under mild oxidation conditions.

EXAMPLE 1 tert-Butyloxycarbonyl-S-p-methoxybenzyl-L-cysteinyl-N-2-chlorobenzyloxycarbonyl-D-lysyl-L-tryptophyl-L-phenylalanyl-L-phenylalanyl-D-tryptophyl-N-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethyl-polystyrene Chloromethylated polystyrene resin 1% cross linked with divinyl benzene (Lab. Systems, Inc.) was esterified with BOC-Cys(SMBzl)OH according to Gisin, *Helv. Chim. Acta*, 56, 1976 (1973). The polystyrene resin ester was treated according to schedule A for the incorporation of BOC-Ser(Bzl)OH, BOC-Thr(Bzl)OH, BOC-Phe-OH, BOC-Thr(Bzl)OH, BOC-Lys(Cl)OH, BOC-D-Trp-OH, BOC-Phe-OH, BOC-Phe-OH, BOC-Trp-OH, BOC-D-Lys(Clz)OH and BOC-Cys(SMBz)OH to afford the title peptidoresins.

Schedule A
1. Wash with $CH_2Cl_2 \times 3$.
2. Treat with TFA-$CH_2Cl_2$-EDT (1:1:5%, v/v) for 5 minutes.
3. Treat as in 2 for 25 minutes.
4. Wash with $CH_2Cl_2 \times 3$.
5. Wash with DMF.
6. Treat with 12% TEA in DMF twice for 3 minutes.
7. Wash with DMF.
8. Wash with $CH_2Cl_2 \times 3$.
9. Treat with 4 equivalents of the corresponding amino acid derivative in $CH_2Cl_2$-DMF and stir for 5 minutes.
10. Add in two portions 5 equivalents of DIC dissolved in $CH_2Cl_2$ and over a period of 30 minutes. Reaction time 6 hours.
11. Wash with DMF$\times 3$.
12. Wash with $CH_2Cl_2 \times 3$.
13. Test ninhydrin reaction according to Kaiser et al., *Annal. Biochem.*, 34, 595, (1970). In case of incomplete reaction repeat lines 9 to 13 as above.

EXAMPLE 2

L-cysteinyl-D-lysyl-L-tryptophyl-L-phenylalanyl-L-phenylalanyl-D-tryptophyl-L-lysyl-L-threonyl-L-phenylalanyl-L-threonyl-L-seryl-L-cysteine cyclic (1-12) disulfide The peptidoresin of the previous example (9 g.) was mixed with anisole (18 ml.) and treated with liquid HF in an ice bath for 45 minutes. The excess HF was removed under vacuo and the residue was taken in 25% aq. AcOH, and filtered. The filtrate was washed with ether and the aqueous phase was poured into 3.5 liters of deaerated water. The pH was brought to 7 with dil. alkali and the disulfhydryl dodecapeptide was oxidized with $K_3Fe(CN)_6$. The excess oxident was removed with ion exchange resin Bio Rad AG 3 and the peptide material was absorbed on a Bio Rex 70 ion exchange resin. Elution with pyridine buffer pH 7 afforded the crude material (500 mg.). This material was chromatographed through Sephadex LH 20 (2.5×150 cm.) and eluted with 10% aq. AcOH. The material which emerged in fractions (5.2 ml. each) 123 to 163 was pooled and lyophilized to yield the title compound (122 mg.). $R_f$ (BWA, 4:1:1)0.54, $R_f$(BWAP, 30:24:6:20)0.76.

Amino acid analysis: Thr(2)1.94, Ser(1)1.01, Phe(3)3, Lys(2)2.09, Trp(1)0.66, Cys(N.D.).

The activity of the product of the preceding preparatory example, (des-Ala$^1$-Gly$^2$, D-Lys$^4$, Trp$^5$, D-Trp$^8$)Somatostatin was determined by the following procedure:

Albino male rats were administered Nembutal intraperitoneally at a dose of 50 milligrams per kilogram. Fifteen minutes later a subcutaneous injection of the test compound or physiological saline was administered. Ten minutes later 0.5 millileters of arginine (300 milligrams per milliliter, pH 7.2) is injected into the heart. Five minutes after receipt of the arginine the rats are decapitated and blood is collected into trasylol-EDTA. An appropriate aliquot was assayed for growth hormone revealing a reduction of growth hormone to 24±7 ng/ml (p<0.01) compared to the control value of 122±26 ng/ml at a dose of 100 micrograms per kilogram. Thus, (des-Ala$^1$-Gly$^2$, D-Lys$^4$, Trp$^5$, D-Trp$^8$)Somatostatin, representative of the corresponding D-Arg$^4$, D-His$^4$, D-Orn$^4$, Phe$^5$, Tyr$^5$, Leu$^5$ and Met$^5$ analogues, their (Ala$^1$-Gly$^2$)somatostatin analogues and the corresponding L-Trp$^8$ and D-Cys$^{14}$ analogues, is an effective agent for selectively reducing secretion of growth hormone at relatively high doses. Each of the compounds of this invention possess a functionally characterizing hydrophilic side chain grouping on the D-amino acid moiety in 4-position and a hydrophobic amino acid in 5-position, which distinguishes them from polypeptides having conventional hydrophilic groupings on the 4-amino acid.

The compounds described herein may be administered to warm blooded mammals, including humans, either intravenously, subcutaneously, intramuscularly or orally to inhibit the release of growth hormone where the host being treated requires therapeutic treatment for excess secretion of somatotropin which is associated with conditions such as juvenile diabetes and acromegaly. The required dosage will vary with the particular condition being treated, the severity of the condition and the duration of treatment. If the active ingredient is administered in tablet form the tablet may contain: a binder such as gum tragacanth, corn starch, gelatin, and excipient such as dicalcium phosphate; a disintegrating agent such as corn starch, alginic acid, etc.; a lubricant such as magnesium stearate; and a sweetening and/or flavoring liquid carriers for intravenous administration include isotonic saline, phosphate buffer solutions, etc.

In addition, the product of Example 2 exhibits antisecretory activity when tested in the four hour plyorus ligated rat test according to the procedure of Shay et al., Gastroenterology, 26, 906–913 (1954). At a dosage between 0.25 and 2.0 mg/kg, an approximate 50% inhibition of total acid output was achieved with statistical significance $p<0.05$. Therefore, the product of Example 2 is also useful as an anti-secretory agent for the treatment of peptic ulcer disease.

What is claimed is:

1. A polypeptide of the formula:

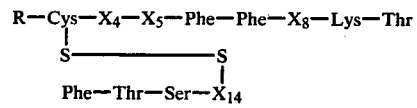

its linear precursor or a non-toxic acid addition salt thereof, in which
R is hydrogen, Ala-Gly, Ala-D-Ala, Gly-Gly, Gly-Gly-Gly, lower alkanoyl or benzoyl;
$X_4$ is D-Lys, D-Arg, D-His or D-Orn;
$X_5$ is Trp, Phe, Tyr, Leu or Met;
$X_8$ is L-Trp or D-Trp; and
$X_{14}$ is Cys or D-Cys.

2. A polypeptide of claim 1 of the formula:

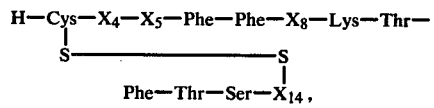

its linear precursor or a non-toxic acid addition salt thereof, in which
$X_4$ is D-Lys, D-Arg, D-His or D-Orn;
$X_5$ is Trp, Phe, Tyr, Leu or Met;
$X_8$ is L-Trp or D-Trp; and
$X_{14}$ is Cys or D-Cys.

3. The polypeptide of claim 2 which is L-cysteinyl-D-lysyl-L-tryptophyl-L-phenylalanyl-L-phenylalanyl-D-tryptophyl-L-lysyl-L-threonyl-L-phenylalanyl-L-threonyl-L-seryl-L-cysteine or a non-toxic acid addition salt thereof.

4. The polypeptide of claim 2 which is L-cysteinyl-D-lysyl-L-tryptophyl-L-phenylalanyl-L-phenylalanyl-D-tryptophyl-L-lysyl-L-threonyl-L-phenylalanyl-L-threonyl-L-seryl-L-cysteine (cyclic 1,12 disulfide) or a non-toxic acid addition salt thereof.

5. The peptido resin which is tert-Butyloxycarbonyl-S-p-methoxybenzyl-L-cysteinyl-N$^\epsilon$-2-chlorobenzyloxycarbonyl-D-lysyl-L-tryptophyl-L-phenylalanyl-L-phenylalanyl-D-tryptophyl-N$^\epsilon$-2-chlorobenzyloxycarbonyl-L-lysyl-O-benzyl-L-threonyl-L-phenylalanyl-O-benzyl-L-threonyl-O-benzyl-L-seryl-S-p-methoxybenzyl-L-cysteinyl-hydroxymethylpolystyrene or a non-toxic acid addition salt thereof.

* * * * *